US011883555B2

(12) United States Patent
Aoki et al.

(10) Patent No.: US 11,883,555 B2
(45) Date of Patent: Jan. 30, 2024

(54) COMPOSITION FOR HARD TISSUE REPAIR AND KIT FOR HARD TISSUE REPAIR

(71) Applicant: Mitsui Chemicals, Inc., Tokyo (JP)

(72) Inventors: Shinya Aoki, Yokohama (JP); Kengo Goto, Ichihara (JP); Takashi Miura, Chiba (JP); Tetsuya Hamada, Ichihara (JP); Ayako Bando, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 2 days.

(21) Appl. No.: 16/499,799

(22) PCT Filed: Mar. 29, 2018

(86) PCT No.: PCT/JP2018/013472
§ 371 (c)(1),
(2) Date: Sep. 30, 2019

(87) PCT Pub. No.: WO2018/181822
PCT Pub. Date: Oct. 4, 2018

(65) Prior Publication Data
US 2020/0030485 A1   Jan. 30, 2020

(30) Foreign Application Priority Data
Mar. 31, 2017   (JP) ................. 2017-072726

(51) Int. Cl.
A61L 24/06     (2006.01)
A61L 24/00     (2006.01)
A61L 24/02     (2006.01)

(52) U.S. Cl.
CPC .......... A61L 24/06 (2013.01); A61L 24/001 (2013.01); A61L 24/02 (2013.01); A61L 2400/06 (2013.01); A61L 2430/02 (2013.01); A61L 2430/06 (2013.01)

(58) Field of Classification Search
None
See application file for complete search history.

(56) References Cited

U.S. PATENT DOCUMENTS

| 4,535,485 | A | 8/1985 | Ashman et al. |
| 5,334,626 | A | 8/1994 | Lin |
| 6,080,801 | A | 6/2000 | Draenert et al. |
| 2002/0156483 | A1 | 10/2002 | Voellmicke et al. |
| 2003/0032964 | A1* | 2/2003 | Watkins .............. A61L 24/0089 606/93 |
| 2004/0157954 | A1 | 8/2004 | Imai et al. |
| 2012/0035296 | A1 | 2/2012 | Nakamura et al. |
| 2012/0225012 | A1* | 9/2012 | Asada .................. A61P 1/06 424/1.11 |
| 2015/0056289 | A1 | 2/2015 | Ueda |

FOREIGN PATENT DOCUMENTS

| EP | 2 502 638 A1 | 9/2012 |
| JP | S59500453 A | 3/1984 |
| JP | H06500718 A | 1/1994 |
| JP | H0678987 A | 3/1994 |
| JP | H08224294 A | 9/1996 |
| JP | 2000254220 A | 9/2000 |
| JP | 2004236729 A | 8/2004 |
| JP | 2004525678 A | 8/2004 |
| JP | 2007197329 A | 8/2007 |
| JP | 2009001536 A | 1/2009 |
| WO | 02/064062 A2 | 8/2002 |
| WO | 2010098305 A1 | 9/2010 |
| WO | 2011062227 A1 | 5/2011 |
| WO | 2013129292 A1 | 9/2013 |
| WO | 2015046100 A1 | 4/2015 |

OTHER PUBLICATIONS

Hernandez et al (Influence of Powder Particle Size Distribution on Complex Viscosity and Other Properties of Acrylic Bone Cement for Vertebroplasty and Kyphoplasty. Inc. J Biomed Mater Res Part B: Appl Biomater 77B: 98-103, 2006). (Year: 2006).*
Koh et al (Effect of storage temperature and equilibration time on polymethyl methacrylate (PMMA) bone cement polymerization in joint replacement surgery. Journal of Orthopaedic Surgery and Research (2015) 10:178) (Year: 2015).*
International Search Report (with English translation) and Written Opinion issued in corresponding International Patent Application No. PCT/JP2018/013471, 10 pages (dated Jul. 3, 2018).
International Search Report (with English translation) and Written Opinion issued in corresponding International Patent Application No. PCT/JP2018/013472, 8 pages (dated Jul. 3, 2018).
K. Goto, "Composition for Hard Tissue Repair and Kit for Hard Tissue Repair," assigned to Mitsui Chemicals, Inc., (filed on Sep. 30, 2019).

* cited by examiner

Primary Examiner — Jake M Vu
(74) Attorney, Agent, or Firm — BUCHANAN INGERSOLL & ROONEY PC

(57) ABSTRACT

Disclosed are: a composition for hard tissue repair with excellent penetrability to an adherend such as a cancellous bone and excellent adhesion to an adherend, which comprises a monomer (A), a polymer (B), a polymerization initiator (C) and a contrast medium (X) having a volume mean particle diameter of 3 μm or more; and a kit for hard tissue repair having members in which the components of the monomer (A), the polymer (B), the polymerization initiator (C) and the contrast medium (X) contained in this composition for hard tissue repair are encased in three or more divided groups in an optional combination.

6 Claims, No Drawings

COMPOSITION FOR HARD TISSUE REPAIR AND KIT FOR HARD TISSUE REPAIR

TECHNICAL FIELD

The present invention relates to a composition for hard tissue repair and a kit for hard tissue repair, with an excellent penetration into an adherend and an excellent adhesion to the adherend, such as a cancellous bone.

BACKGROUND ART

Various compositions for hard tissue repair have been investigated as a bone cement for fixing hard tissue, such as bones and cartilages, to an artificial joint; a bone filler used for treating osteoporosis; and an artificial bone material. For example, a composition containing polymethyl methacrylate, methyl methacrylate, and benzoyl peroxide (polymerization initiator); as well as a composition containing a (meth)acrylate, an inorganic filler, such as calcium phosphate, and an organic peroxide; have been investigated (for example, Patent Document 1). However, such compositions cause large heat generation upon curing, and have a high risk of damaging the affected tissue.

As a composition for hard tissue repair which has improved the above point, for example, Patent Document 2 discloses a composition for hard tissue repair containing a (meth)acrylate (A), a (meth)acrylate polymer (B), a specific polymerization initiator (C) and a contrast medium (X). This composition generates a little heat upon curing and is also excellent in workability.

RELATED ART DOCUMENTS

Patent Documents

Patent Document 1: Japanese Unexamined Patent Application Publication (JP-A) No. 8-224294; JP. 08-224294 (1996)
Patent Document 2: International Publication WO 2011/062227

SUMMARY OF THE INVENTION

Technical Problem

The present inventors considered that there was still room for improvement on the conventional compositions for hard tissue repair, from the viewpoint of macroscopic adhesion with bone tissue. For example, if the penetration of a bone cement (a composition for hard tissue repair) into a cancellous bone is inferior, a gap is formed at the interface with the bone to cause pain due to osteolysis, and if it gets worse, revision surgery will be required. Such a problem is very important in the present field.

Therefore, an object of the present invention is to provide a composition for hard tissue repair and a kit for hard tissue repair with an excellent penetration into an adherend and an excellent adhesion to the adherend such as cancellous bond.

Solution to Problem

The present inventors have intensively investigated to achieve the above-described object and resultantly found that adhesion to bone tissue was improved by using a contrast medium (X) having a volume mean particle diameter in a specific range. The present inventors have completed the present invention based on the above new finding, i.e., the present invention is defined by the following matters:

[1] A composition for hard tissue repair comprising a monomer (A), a polymer (B), a polymerization initiator (C) and a contrast medium (X) having a volume mean particle diameter of 3 µm or more.
[2] The composition for hard tissue repair according to [1], wherein the simulated bone penetrability as measured by the following method is 1.0 mm or more:
[Method of Measuring Simulated Bone Penetrability]
A simulated bone penetrability is measured by impregnating a polyurethane foam having open cell porous (porosity 95%) with physiological saline, putting the composition on the polyurethane impregnated with the physiological saline at 5 minutes after the composition becomes a soft mass and has no more stringiness, applying a pressure load of 75 kPa for 30 seconds to the composition on the polyurethane, measuring the penetration depth (mm) of the composition into the polyurethane foam.
[3] The composition for hard tissue repair according to [1], wherein the contrast medium (X) is barium sulfate or zirconia.
[4] The composition for hard tissue repair according to [1], wherein the monomer (A) is a (meth) acrylate-based monomer.
[5] The composition for hard tissue repair according to [1], wherein the polymer (B) is a (meth)acrylate-based polymer.
[6] The composition for hard tissue repair according to [1], comprising 10 to 45 parts by mass of the monomer (A), 54.9 to 80 parts by mass of the polymer (B) and 0.1 to 10 parts by mass of the polymerization initiator (C) (the sum of the components (A) to (C) is taken as 100 parts by mass), and 0.5 to 70 parts by mass of the contrast medium (X).
[7] The composition for hard tissue repair according to [1], wherein the volume mean particle diameter of the contrast medium (X) is 3.0 to 25.1 µm.
[8] The composition for hard tissue repair according to [1], wherein the volume mean particle diameter of all particles contained in the composition for hard tissue repair is 32 µm or less.
[9] A kit for hard tissue repair comprising three or more members, in which each of the components of the monomer (A), the polymer (B), the polymerization initiator (C) and the contrast medium (X) of the composition for hard tissue repair according to [1] are divided and contained in the members in an optional combination.

Advantageous Effects of Invention

According to this invention, a composition for hard tissue repair and a kit for hard tissue repair with an excellent penetration into an adherend and an excellent adhesin to the adherend, such as a cancellous bone, can be provided.

According to a general common knowledge, when a constant medium passes through a gap, the constant medium having a smaller particle diameter is expected to pass through the gap more easily. However, it is surprising according to the present invention that the simulated bone penetrability of the composition for hard tissue repair is improved, by using a contrast medium (X) having a relatively large particle diameter. Although the reason for this phenomenon is not entirely clear, one reason is presumed that, when the particle diameter of the contrast medium (X)

is small, the powders tend to cause aggregation and form large aggregate particles, while the simulated bone penetrability would be improved when the particle diameter of the contrast medium (X) is large, because the contrast medium is difficult to form aggregates.

DESCRIPTION OF EMBODIMENTS

[Monomer (A)]

The monomer (A) used in the present invention is not particularly limited as long as the monomer can be polymerized by the polymerization initiator (C) described later. As the monomer (A), any one of monofunctional monomers and polyfunctional monomers can be used depending on the purpose of use.

As the monomer (A), for example, (meth)acrylate-based monomers and other vinyl compounds can be used. Among them, (meth)acrylate-based monomers are preferable in terms of relatively low stimulation to the human body. In the present invention, "(meth)acrylate" is a generic term for acrylate and methacrylate. In general, a monomer having an acidic group is excellent in adhesion to a hard tissue. Since the monomer having an acidic group acts also as a decomplexing agent described later, polymerization reaction can be initiated by using the monomer having an acidic group, when an alkylborane-amine complex is used as a polymerization initiator (C). Thus, for example, the adhesion can also be improved by using an appropriate amount of a monomer having an acidic group in combination with a (meth)acrylate-based monomer having no acidic group.

Concrete examples of the monofunctional (meth)acrylate-based monomer having no acidic group include (meth)acrylic acid alkyl esters such as methyl (meth)acrylate, ethyl (meth)acrylate, propyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate and isobornyl (meth)acrylate; hydroxyalkyl esters of (meth)acrylic acid such as 2-hydroxyethyl (meth)acrylate, 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth) acrylate, 1,2-dihydroxypropyl mono(meth)acrylate, 1,3-dihydroxypropyl mono(meth)acrylate and erythritol mono(meth)acrylate; polyalkylene glycol mono(meth)acrylates such as diethylene glycol mono(meth)acrylate, triethylene glycol mono(meth)acrylate, polyethylene glycol mono(meth)acrylate and polypropylene glycol mono(meth)acrylate; (poly)alkylene glycol monoalkyl ether (meth)acrylates such as ethylene glycol monomethyl ether (meth)acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate and polypropylene glycol monoalkyl ether (meth)acrylate; fluoroalkyl esters of (meth)acrylic acid such as perfluorooctyl (meth)acrylate and hexafluorobutyl (meth)acrylate; silane compounds having a (meth)acryloxyalkyl group such as γ-(meth)acryloxypropyltrimethoxysilane and γ-(meth)acryloxypropyltri(trimethylsiloxy) silane; and, (meth)acrylates having a hetero ring such as tetrahydrofurfuryl (meth)acrylate.

Concrete examples of the polyfunctional (meth)acrylate-based monomer having no acidic group include poly(meth)acrylates of polyalkane polyols such as ethylene glycol di(meth)acrylate, propylene glycol di(meth)acrylate, butylene glycol di(meth)acrylate, neopentyl glycol di(meth)acrylate, hexylene glycol di(meth)acrylate, trimethylolpropane tri(meth)acrylate and pentaerythritol tetra(meth)acrylate; polyoxyalkane polyol poly(meth)acrylates such as diethylene glycol di(meth)acrylate, triethylene glycol di(meth)acrylate, polyethylene glycol di(meth)acrylate, dipropylene glycol di(meth)acrylate, polypropylene glycol di(meth)acrylate, dibutylene glycol di(meth)acrylate and dipentaerythritol hexa(meth)acrylate; alicyclic or aromatic di(meth)acrylates represented by the following general formula (1):

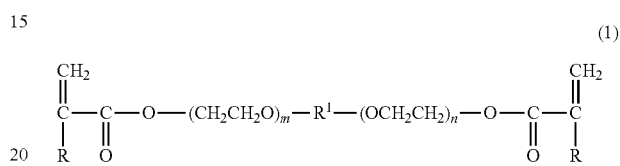

(in formula (1), R is a hydrogen atom or a methyl group, m and n are each independently a number of 0 to 10, and $R^1$ is any one of

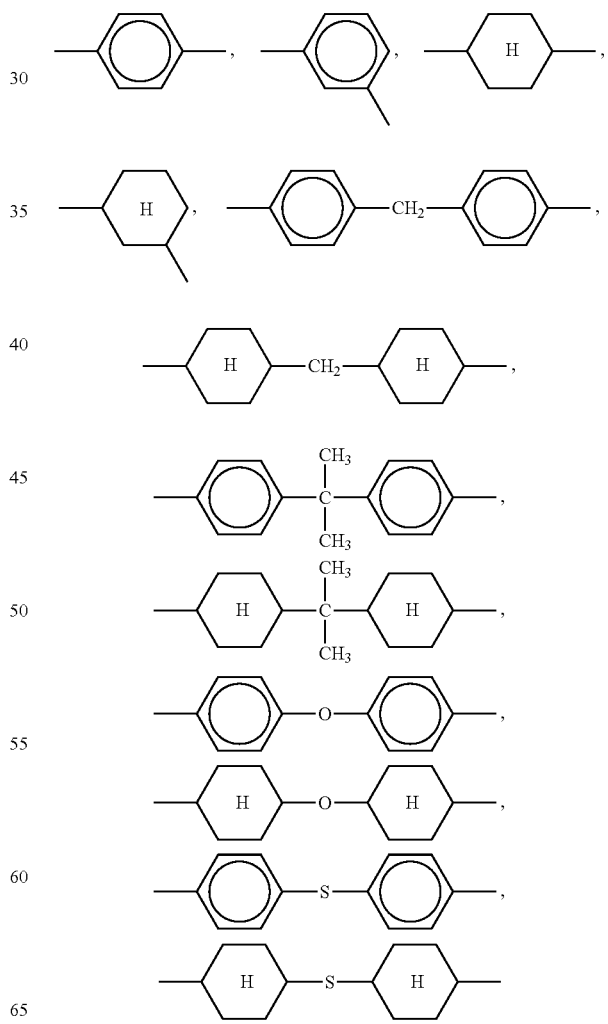

alicyclic or aromatic epoxy di(meth)acrylates represented by the following general formula (2):

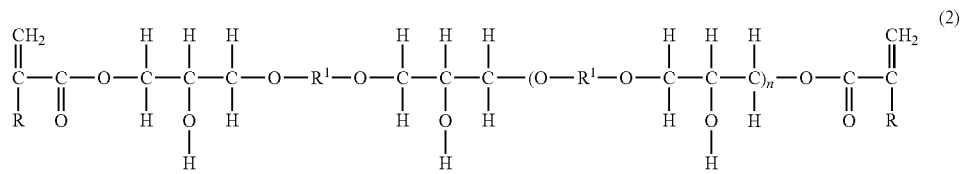

(in the formula (2), R, n and $R^1$ have the same meaning as R, n and $R^1$ in the above-described formula (1)); and polyfunctional (meth)acrylates having a urethane bond in the molecule represented by the following formula (3):

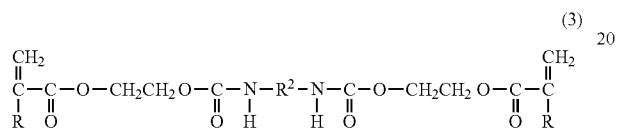

(in the formula (3), R has the same meaning as R in the above-described formula (1), and $R^2$ is any one of

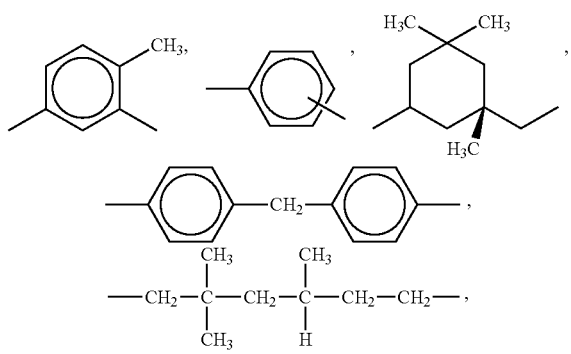

-continued

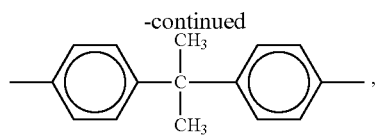

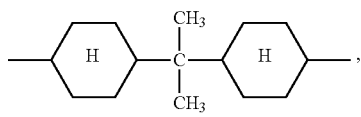

In the above concrete example compounds, preferable monofunctional (meth)acrylate-based monomers include alkyl (meth)acrylates such as methyl (meth)acrylate and ethyl (meth)acrylate; hydroxyalkyl esters of (meth)acrylic acid such as 2-hydroxyethyl (meth)acrylate, 1,3-dihydroxypropyl mono(meth)acrylate and erythritol mono(meth)acrylate; and polyethylene glycol mono (meth)acrylates such as triethylene glycol monomethyl ether (meth)acrylate and triethylene glycol mono(meth)acrylate.

In the above concrete example compounds, preferable polyfunctional (meth)acrylate-based monomers include di(meth)acrylates having an ethylene glycol chain in the molecule such as triethylene glycol di(meth)acrylate and polyethylene glycol di(meth)acrylate; compounds represented by the following formula (1)-a:

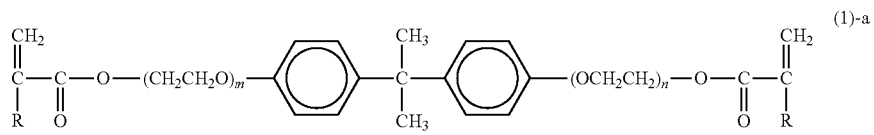

(in the formula (1)-a, R, m and n have the same meaning as R, m and n in the above-described formula (1));

compounds represented by the following formula (2)-a:

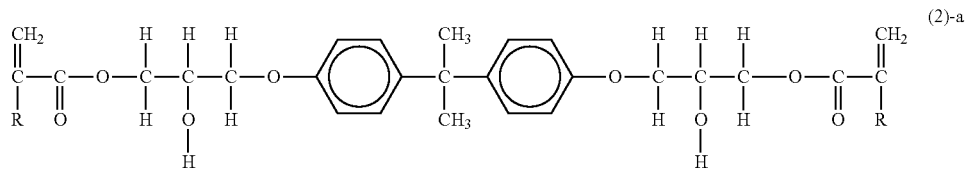

(in formula (2)-a, R has the same meaning as R in the above-described formula (1)); and compounds represented by the following formula (3)-a:

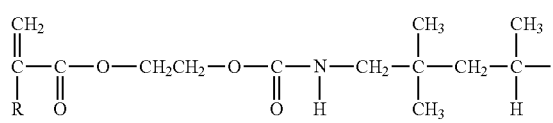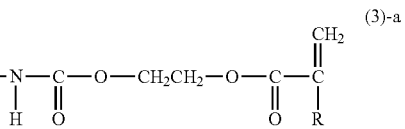

(3)-a (in the formula (3)-a, R is the same as R in the above-described formula (1)).

Two or more of these (meth)acrylate-based monomers may be used in combination.

Concrete examples of the monomer having an acidic group(s), i.e., the acidic group-containing monomer, include monomers having a carboxylic acid group(s) or an anhydride group(s) thereof such as (meth)acrylic acid and an anhydride thereof, 1,4-di(meth)acryloxyethylpyromellitic acid, 6-(meth)acryloxyethylnaphthalene-1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl-4-aminosalicylic acid, 4-(meth)acryloxyethyltrimellitic acid and an anhydride thereof, 4-(meth)acryloxybutyltrimellitic acid and an anhydride thereof, 4-(meth)acryloxyhexyltrimellitic acid and an anhydride thereof, 4-(meth)acryloxydecyltrimellitic acid and an anhydride thereof, 2-(meth)acryloyloxybenzoic acid, 3-(meth)acryloyloxybenzoic acid, 4-(meth)acryloyloxybenzoic acid, β-(meth)acryloyloxyethyl hydrogen succinate, β-(meth)acryloyloxyethyl hydrogen maleate, β-(meth)acryloyloxyethyl hydrogen phthalate, 11-(meth)acryloyloxy-1,1-undecanedicarboxylic acid and p-vinylbenzoic acid; monomers having a phosphate group such as (2-(meth)acryloxyethyl) phosphoric acid, (2-(meth) acryloxyethylphenyl) phosphoric acid and 10-(meth)acryloxydecylphosphoric acid; and monomers having a sulfonate group such as p-styrenesulfonic acid and 2-acrylamide-2-methylpropanesulfonic acid.

In the above monomers, 4-methacryloxyethyl trimellitic acid and an anhydride thereof are preferable.

Two or more of the acidic group-containing monomers may be used in combination. The acidic group-containing monomers can also be used as a calcium salt.

The blending amount of the monomer (A) is preferably 10 to 45 parts by mass, more preferably 20 to 45 parts by mass, particularly preferably 25 to 36 parts by mass (based on the sum of the components (A) to (C) taken as 100 parts by mass). The lower limit value of each of the above ranges is significant in terms of coating easiness, handling and penetration into bone tissue, etc. The upper limit is significant in terms of adhesive strength and mechanical properties. If the monomer (A) comprises an acid group-containing monomer(s), the amount of the acid group-containing monomer(s) is preferably 0.01 to 20% by mass with respect to the whole amount of the monomer (A), i.e., with respect to 100% by mass of the sum of the monomer (A).

[Polymer (B)]

Although the type of the polymer (B) used in the present invention is not particularly limited, it is preferable that a part or all of the monomer units forming the polymer (B) originate from the same kind of monomers as a part or all of the monomer (A) as described above. In the present invention, "the polymer" is a general term for homopolymers and copolymers. As the polymer (B), for example, (meth)acrylate-based polymers and other vinyl polymers can be used. Among them, (meth)acrylate-based polymers are preferable.

Concrete examples of the (meth)acrylate-based polymer include non-crosslinked polymers such as polymethyl (meth)acrylate, polyethyl (meth)acrylate, methyl (meth)acrylate-ethyl (meth)acrylate copolymer, methyl (meth)acrylate-butyl (meth)acrylate copolymer and methyl (meth)acrylate-styrene copolymer; cross-linked polymers such as methyl (meth)acrylate-ethylene glycol di(meth)acrylate copolymer, methyl (meth)acrylate-triethylene glycol di(meth)acrylate copolymer and methyl (meth)acrylate-butadiene-based monomer copolymer, and these polymers partially forming a calcium salt.

The polymer may be an organic/inorganic composite in which a metal oxide or a metal salt is coated with a non-crosslinked polymer or a crosslinked polymer.

The form of the polymer (B) is not particularly limited, but the polymer (B) in a powder form is preferable. As the polymer powder, one kind of polymer powder may be used alone, or a mixture of two or more kinds of polymer powders may be used. Particularly, it is preferable to use a mixture of two or more kinds of polymer powders having different specific surface areas and/or volume mean particle diameters.

The shape of each particle of the polymer powder to be used as the polymer (B) may be either spherical shape, or amorphous or indefinite shape, but it is preferable to use a mixture of a polymer powder of spherical particles and a polymer powder of indefinite shape particles. Since spherical particles have a relatively small specific surface area, while indefinite shape particles have a relatively large specific surface area, they can be distinguished by the difference in their specific surface areas. According to the present invention, it is preferable to use a polymer powder (b1) with a specific surface area of 0.05 to 0.5 $m^2/g$ as the spherical shape polymer powder, and a polymer powder (b3) with a specific surface area of 1.5 to 4.5 $m^2/g$ as the indefinite shape powder. Furthermore, it is also preferable to use, together with them, polymer particles (b2) having a specific surface area of 0.51 to 1.2 $m^2/g$, which have an intermediate particle shape between the spherical particle shape of the polymer powder (b1) and the indefinite shape particles of the polymer powder (b3). The method of measuring a specific surface area is described later in the section "Examples".

The specific surface area of the polymer powder (b1) is 0.05 to 0.5 $m^2/g$, preferably 0.1 to 0.4 $m^2/g$. The specific surface area of the polymer powder (b2) is 0.51 to 1.2 $m^2/g$, preferably 0.7 to 1.1 $m^2/g$. The specific surface area of the polymer powder (b3) is 1.5 to 4.5 $m^2/g$, preferably 2.5 to 3.5 $m^2/g$.

The weight average molecular weight of the polymer powder (b1) is preferably 10,000 to 5,000,000, more preferably 50,000 to 1,540,000, particularly preferably 100,000 to 500,000. The weight average molecular weight of the polymer powder (b2) is preferably 10,000 to 5,000,000, more preferably 50,000 to 1,660,000, particularly preferably 100,000 to 500,000. The weight average molecular weight of the polymer powder (b3) is preferably 150,000 to 5,000,000, more preferably 200,000 to 1,150,000, particularly preferably 240,000 to 670,000.

The method of measuring the weight average molecular weight is described later in the section of "Examples". The weight average molecular weight is measured as a standard polystyrene-equivalent value measured by gel permeation chromatography (GPC).

The volume mean particle diameter of the polymer powder (b1) is preferably 12.7 to 77 μm, more preferably 15 to 45 μm, particularly preferably 17.5 to 35 μm. The volume mean particle diameter of the polymer powder (b2) is preferably 1 to 15 μm, more preferably 3.5 to 10 μm. The volume mean particle diameter of the polymer powder (b3) is preferably 0.3 to 60 μm, more preferably 7.5 to 50 μm, particularly preferably 15.7 to 40 μm. The method of measuring the volume mean particle diameter is described later in the section "Examples".

The weight average molecular weight of the polymer (B) (when one kind of polymer is used alone as a single component, the weight average molecular weight of the polymer used alone is adopted, while, when a mixture of two or more kinds of polymers is used, the weight average molecular weight of the entire mixture is adopted) is preferably 50,000 to 5000,000, more preferably from 75,000 to 2,000,000, particularly preferably 75,000 to 880,000, most preferably 100,000 to 400,000. When the polymer (B) is a polymer powder, the volume mean particle diameter of the polymer powder (when one kind of powder is used alone, the volume mean particle diameter thereof is adopted, while, when a mixture of two or more kinds of powders is used, the volume mean particle diameter of the entire mixture is adopted) is preferably 10 to 80 μm, more preferably 15 to 45 μm, particularly preferably 15 to 30 μm.

The blending amount of the polymer (B) is preferably 54.9 to 80 parts by mass, more preferably 56.7 to 73.7 parts by mass, particularly preferably 59.7 to 70.7 parts by mass (the sum of the components (A) to (C) is taken as 100 parts by mass). The amount of the polymer powder (b1) in 100% by mass of the polymer (B) is preferably 50.5 to 95% by mass, more preferably 53 to 85% by mass. The amount of the polymer powder (b2) is preferably 0 to 33.5% by mass, more preferably 0 to 25% by mass. The amount of the polymer powder (b3) is preferably from 5 to 49.5% by mass, more preferably 15 to 47% by mass.

The content of the polymer powder having a volume mean particle diameter of more than 2.0 μm in the polymer (B) is preferably more than 70% by mass, more preferably 80% by mass or more, particularly preferably 90% by mass or more.

[Polymerization Initiator (C)]

The polymerization initiator (C) used in the present invention is not particularly limited, and various known compounds can be used. Among them, organic peroxides and organic boron compounds are preferable, and organic boron compounds are particularly preferred.

The organic peroxide includes, for example, diacyl peroxides such as diacetyl peroxide, diisobutyl peroxide, didecanoyl peroxide, benzoyl peroxide (BPO) and succinic acid peroxide; peroxydicarbonates such as diisopropylperoxydicarbonate, di-2-ethylhexylperoxydicarbonate and diallylperoxydicarbonate; peroxyesters such as tert-butylperoxy isobutyrate, tert-butyl peroxy neodecanate and cumene peroxy neodecanate; and peroxy sulfonates such as acetylcyclohexylsulfonyl peroxid.

The organic peroxide may be used as a redox initiator in combination with a tertiary amine or with a tertiary amine and either sulfinic acid or its alkali metal salt. Among them, benzoyl peroxide (BPO) combined with N,N-dimethyl-p-toluidine, and, benzoyl peroxide (BPO) combined with N,N-dihydroxyethyl-p-toluidine, are preferable.

Tertiary amine(s) such as N,N-dimethyl-p-toluidine and N,N-dihydroxyethyl-p-toluidine are preferably added to the monomer (A) prior to use. The addition amount thereof is preferably 5.0 parts by mass or less, more preferably 0.1 to 3.0 parts by mass, particularly preferably 0.25 to 2.6 parts by mass (the sum of the monomer (A) and the tertiary amine is taken as 100 parts by mass). When the tertiary amine is used, the polymerization reaction can be initiated easily without heating, since radicals are generated by electron transfer even at room temperature.

As the organic boron compound, for example, trialkylboron, alkoxyalkylboron, dialkylborane, partially oxidized trialkylboron and alkylborane-amine complex can be used.

Concrete examples of the trialkylboron include trialkylborons having an alkyl group(s) having 2 to 8 carbon atoms such as triethylboron, tripropylboron, triisopropylboron, tributylboron, tri-sec-butylboron, triisobutylboron, tripentylboron, trihexylboron, triheptylboron, trioctylboron, tricyclopentylboron and tricyclohexylboron.

The alkyl group may be any one of a linear alkyl group, a branched alkyl group or a cycloalkyl group, and three alkyl groups contained in trialkylboron may be the same or different.

Concrete examples of the alkoxyalkylboron include monoalkoxydialkylborons such as butoxydibutylboron; and dialkoxymonoalkylborons. The alkyl group of the alkoxyalkylboron and the alkyl portion of its alkoxy group may be the same or different.

Concrete examples of the dialkylborane include dicyclohexylborane and diisoamylborane. Two alkyl groups of the dialkylborane may be the same or different. Two alkyl groups contained in the dialkylborane may be connected to form a monocyclic structure or a bicyclo structure. Such compounds include, for example, 9-borabicyclo [3.3.1] nonane.

The partially oxidized trialkylboron is a partial oxide compound of a trialkylboron. Among them, partially oxidized tributylboron is preferable. The amount of oxygen to be added with respect to 1 mol of a trialkylboron is preferably 0.3 to 0.9 mol, more preferably 0.4 to 0.6 mol.

Concrete examples of the alkylborane-amine complexes include triethylborane-diaminopropane (TEB-DAP), triethylborane-diethylenetriamine (TEB-DETA), tri-n-butylborane-3-methoxypropylamine (TnBB-MOPA), tri-n-butylbotane-diaminopropane (TnBB-DAP), tri-sec-butylborane-diaminopropane (TsBB-DAP), methylaminoethoxydiethylborane (MAEDEB), methylaminoethoxydicyclohexylborane (MAEDCB) and derivatives derived from them. These alkylborane-amine complexes can be used alone, or two or more complexes can be used in combination.

When the alkylborane-amine complex is used as the polymerization initiator (C), it is preferred to additionally use a decomplexing agent together with the monomer (A). This "decomplexing agent" means a compound which is capable of releasing an alkylborane from the alkylborane-amine complex, and permits the initiation of the polymerization reaction by release of the alkylborane.

As a suitable decomplexing agent, for example, any acid or monomer having an acid group(s) (the above-mentioned monomer(s) having an acid group(s) used as the monomer (A)) can be used. Preferred acids include Lewis acids (e.g., $SnCl_4$, $TiCl_4$) and Broensted acids (e.g., carboxylic acids, HCl, $H_2SO_4$, $H_3PO_4$, phosphonic acid, phosphinic acid, silicic acid). Suitable carboxylic acids include those represented by the general formula R—COOH. In the formula, R represents a hydrogen atom, an alkyl group having 1 to 8 carbon atoms (preferably an alkyl group having 1 to 4 carbon atoms), an alkenyl group having 2 to 8 carbon atoms (preferably an alkenyl group having 2 to 4 carbon atoms), an alkynyl group having 2 to 8 carbon atoms (preferably an alkynyl group having 2 to 4 carbon atoms), or an aryl group having 6 to 10 carbon atoms (preferably an aryl group having 6 to 8 carbon atoms). The alkyl group, the alkenyl group and the alkynyl group represented by R may be linear or branched. The aliphatic group in R may be saturated or unsaturated. The aryl group in R may be substituted with a substituent such as an alkyl group, an alkoxy group or a halogen atom, or may be un-substituted.

Concrete examples of the carboxylic acid represented by the above-described general formula include acrylic acid, methacrylic acid, acetic acid, benzoic acid and p-methoxybenzoic acid. As specific examples of the monomer having an acidic group(s), 4-methacryloxyethyltrimellitic acid and an anhydride thereof are preferable, among the above-mentioned monomer (A).

Among the organic boron compounds, tributylboron and partially oxidized tributylboron are preferred, and, particularly, partially oxidized tributylboron is more preferable. When tributylboron and/or partially oxidized tributylboron are used as the organic boron compound, not only the operability is improved, but also there is tendency to provide appropriate reactivity to a living organism containing water. In addition, when tributylboron and/or partially oxidized tributylboron are used as the organic boron compound, the reaction starts even at a place with a large amount of water such as living organisms, and the reaction proceeds. As a result, the monomer rarely remains at the interface between an adhesive and the living organism, and harm against the living organism in such situation is extremely little.

These organic boron compounds can be used alone, or two or more organic boron compounds can be used in combination.

The organic boron compound may further contain an aprotic solvent. When the organic boron compound is diluted with an aprotic solvent, the heat buildup of the pyrophoric organic boron compound becomes milder, its pyrophoricity is suppressed, and the handling during transport, storage and mixing treatment becomes easier. Further, since rapid heat generation can be suppressed, even when a very large amount of a composition for hard tissue repair is used, damage to the tissue in contact with the composition for hard tissue repair tends to be reduced.

The boiling point at one atmosphere pressure (1 atm) of the aprotic solvent is usually 30° C. to 150° C., preferably 50° C. to 120° C. When the boiling point is less than the above range, there is a tendency that the aprotic solvent volatilizes or scatters from the polymerization initiator during transportation or storage, and its ignition suppression effect against the organic boron compound is reduced. In contrast, when the boiling point exceeds the above range, there is a tendency that the aprotic solvent remains in large amount on the cured product formed from the composition for hard tissue repair of the present invention, and the adhesive strength of the cured product to the affected area, and physical properties such as flexural modulus, tensile strength, compressive strength and flexural strength become poor.

As the aprotic solvent, a solvent which does not have a group comprising an active hydrogen such as a hydroxy group or a mercapto group which reacts with an organic boron compound and which can form a homogeneous solution with the organic boron compound is preferable.

Examples of the aprotic solvent include hydrocarbons such as pentane, hexane, cyclohexane, heptane, benzene and toluene; halogenated hydrocarbons such as fluorobenzene, 1,1-dichloroethane, 1,2-dichloroethane and flon, i.e., fluorocarbon, ethers such as diethyl ether, diisopropyl ether, ethylene glycol dimethyl ether and tetrahydrofuran; ketones such as acetone, methyl ethyl ketone and diethyl ketone; and esters such as methyl acetate, ethyl acetate and isopropyl acetate. Among them, saturated aliphatic hydrocarbons such as pentane, hexane and heptane, ethers and esters are preferable. Hexane, diisopropyl ether and ethyl acetate are more preferable. These aprotic solvents can be used alone, or two or more aprotic solvents can be used in combination.

The content of the aprotic solvent is preferably 30 to 80 parts by mass with respect to 100 parts by mass of the organic boron compound. When the content of the aprotic solvent is less than the above range, a sufficient dilution effect cannot be obtained, and the effect of suppressing heat generation or ignition tends to be insufficient. In contrast, when the content of the aprotic solvent exceeds the above range, the polymerization initiation ability of the polymerization initiator (C) tends to be reduced.

The organic boron compound may contain an alcohol in addition to or in place of the aprotic solvent. By adding an alcohol to the organic boron compound, there is a tendency that the reaction by the organic boron compound becomes further milder without reducing the polymerization activity, and burning and firing are suppressed when the organic boron compound comes into contact with a material such as paper in the air.

The boiling point of the alcohol at 1 atm is usually 60° C. to 180° C., preferably 60° C. to 120° C. When the boiling point is less than the above range, there is a tendency that the alcohol volatilizes and scatters from the polymerization initiator composition during transportation or storage, and its ignition suppression effect against the organic boron compound is reduced. In contrast, when the boiling point exceeds the above range, the curing time of the composition for hard tissue repair tends to be long, and the adhesive strength of the cured product to the affected area and the physical properties such as flexural modulus, tensile strength, compressive strength and flexural strength tend to become poor.

Concrete examples of the alcohol include methanol, ethanol, n-propanol and isomers thereof, n-butanol and isomers thereof, n-pentanol and isomers thereof, n-hexanol and isomers thereof, and n-heptanol and isomers thereof. Among them, alcohols having 4 or less carbon atoms, i.e., methanol, ethanol, n-propanol and isomers thereof, and n-butanol and isomers thereof are preferable, and ethanol and n-propanol are more preferable. These alcohols can be used alone, or two or more alcohols can be used in combination.

The content of the alcohol is usually 0.01 to 40 parts by mass, preferably 0.1 to 30 parts by mass, more preferably 0.5 to 20 parts by mass with respect to 100 parts by mass of the organic boron compound. When the content of the alcohol is less than the above range, there is a tendency that the sufficient dilution effect is not obtained and the effect of suppressing heat generation or firing becomes insufficient. In contrast, when the content of the alcohol exceeds the above range, the polymerization initiation ability of the polymerization initiator tends to be lowered more than that needed.

When an alcohol and an aprotic solvent are used in combination, the content of the aprotic solvent is preferably 5 to 40 parts by mass, more preferably 10 to 30 parts by mass, particularly preferably 10 to 25 parts by mass with respect to 100 parts by mass of the organic boron compound. When the content of the aprotic solvent is less than the above range, the effect of suppressing heat generation or ignition tends to be insufficient. In contrast, when the content of the aprotic solvent exceeds the above range, the polymerization initiation ability of the polymerization initiator (C) tends to be reduced.

The blending amount of the polymerization initiator (C) is preferably 0.1 to 10 parts by mass, more preferably 1.0 to 7.0 parts by mass, particularly preferably 2.1 to 4.3 parts by mass with respect to 100 parts by mass of the sum of the monomer (A), the polymer (B) and the polymerization initiator (C). When the blending amount of the polymerization initiator (C) is less than the above range, there is a tendency that the polymerization does not progress easily and the hardening time becomes late. In contrast, when the blending amount of the polymerization initiator (C) exceeds the above range, there is a possibility that viscosity lowers by dilution and there is a possibility that safety is adversely affected, and further, it is also presumed that a cured polymerization product is formed quickly by rapid progress of polymerization.

[Contrast Medium (X)]

The volume mean particle diameter of the contrast medium (X) used in the present invention is 3 μm or more, preferably 3.0 to 25.1 μm, more preferably 3.0 to 18.0 μm, particularly preferably 3.5 to 15.5 μm, most preferably 4.0 to 13.0 μm. It is considered that the contrast medium (X) having such a relatively large volume mean particle diameter is difficult to cause aggregation, and, as a result, the penetration of the composition into a cancellous bone is improved, and the adhesion to the adherend is excellent. The method of measuring the volume mean particle diameter is described later in the section of "Examples".

The type of the contrast medium (X) is not particularly limited. Concrete examples thereof include barium sulfate, zirconia, bismuth carbonate, calcium tungstate, ytterbium and iodine compounds. Among them, barium sulfate and zirconia are preferable in terms of use for hard tissue, particularly actual use for a bone cement. A contrast medium (X) which is able to independently form particles is preferable. In addition, it is preferable that the surfaces of the particles are not coated (for example, not coated with titanium dioxide).

The blending amount of the contrast medium (X) is preferably 0.5 to 70 parts by mass, more preferably 0.5 to 45 parts by mass, particularly preferably 2.5 to 33.8 parts by mass, most preferably from 4.5 to 22.5 parts by mass with respect to 100 parts by mass of the sum of the monomer (A), the polymer (B) and the polymerization initiator (C).

It is preferable that the contrast medium (X) is not enclosed and/or adsorbed inside of the polymer (B) and that the contrast medium (X) is dispersed in the liquid components (the monomer (A), the polymerization initiator (C), etc.) before curing, when the composition for hard tissue repair is prepared. It is preferable that 80% by mass or more of the contrast medium (X) is dispersed in the liquid components. It is more preferable that 90% by mass or more is dispersed in the liquid components. It is particularly preferable that 95% by mass or more is dispersed in the liquid components. It is most preferable that 99% by mass or more is dispersed in the liquid components.

It is preferable that the contrast medium (X) is not enclosed and/or adsorbed in inside the polymer (B). The amount of the contrast medium (X) enclosed and/or adsorbed inside of the polymer (B) to the entire contrast medium (X) is preferably 20% by mass or less, more preferably 10% by mass or less, particularly preferably 1% by mass or less, most preferably 0.1% by mass or less.

It is desirable that 50% by mass or more of the liquid components contained in the composition for hard tissue repair of the present invention are the monomer (A). It is further preferable that, in the liquid components, 60% by mass or more are the monomer (A), more preferably 70% by mass or more are the monomer (A), particularly preferably 80% by mass or more are the monomer (A), most preferably 90% by mass or more are the monomer (A).

The content of water in the liquid components (excluding liquid in the polymer (B)) contained in the composition for hard tissue repair of the present invention is desirably 20% by mass or less, preferably 10% by mass or less, more preferably 5.0% by mass or less, particularly preferably 3.0% by mass or less, most preferably 1.5% by mass or less.

The content of water in all liquid components contained in the composition for hard tissue repair of the present invention is desirably 25% by mass or less, preferably 15% by mass or less, more preferably 10% by mass or less, particularly preferably 5.0% by mass or less, most preferably 3.0% by mass or less.

[Other Ingredients]

The composition for hard tissue repair of the present invention may contain a polymerization inhibitor, if necessary. Concrete examples of the polymerization inhibitor include hydroquinone compounds such as hydroquinone and dibutyl hydroquinone; phenols such as hydroquinone monomethyl ether, 2,6-di-tert-butylphenol and 2,6-di-tert-butyl-p-cresol; catechol; pyrogallol; benzoquinone; 2-hydroxybenzoquinone; p-methoxyphenol; t-butylcatechol; butylated hydroxy anisole; butylated hydroxytoluene; and t-butylhydroquinone. Among them, a mixture of hydroquinone monomethyl ether and 2,6-di-tert-butyl-p-cresol is preferable. In addition, hydroquinone monomethyl ether may be preferable in terms of its own stability. The polymerization inhibitors can be used alone or, two or more polymerization inhibitors can be used in combination.

The amount of the polymerization inhibitor added is preferably 1 to 1500 ppm, more preferably 5 to 1000 ppm, and particularly preferably 5 to 500 ppm, based on the entire amount of the composition for hard tissue repair. The addition amount of the polymerization inhibitor (D) is 10 to 5000 ppm, more preferably 25 to 1000 ppm, particularly preferably 25 to 500 ppm with respect to the monomer (A).

The composition for hard tissue repair of the present invention may contain an ultraviolet absorber, if necessary.

Concrete examples of the ultraviolet absorbers include: benzotriazole compounds such as 2-(2'-hydroxy-5'-methylphenyl) benzotriazole, 2-(3',5'-di-tert-butyl-2'-hydroxyphenyl) benzotriazole, 2-(5'-tert-butyl-2'-hydroxyphenyl) benzotriazole, 2-(2'-hydroxy-5'-(1,1,3,3-tetramethylbutyl) phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl) benzotriazole, 2-(3'-tert-butyl-2'-hydroxy-5'-(2-octyloxycarbonylethyl) phenyl)-5-chlorobenzotriazole, 2-(3'-tert-butyl- 5'-[2-(2-ethylhexyloxy) carbonylethyl]-2'-hydroxyphenyl)-5-chlorobenzotriazole, 2-(3'-tert-butyl-2'-hydroxy-5'-(2-methoxycarbonylethyl) phenyl)-5-chlorobenzotriazole, 2-(3'-tert-butyl-2'-hydroxy-5'-(2-methoxycarbonylethyl) phenyl) benzotriazole, 2-(3'-tert-butyl-2'-hydroxy-5'-(2-octyloxycarbonylethyl) phenyl) benzotriazole, 2-(3'-tert-butyl-5'-[2-(2-ethylhexyloxy) carbonylethyl]-2'-hydroxyphenyl) benzotriazole, 2-(3'-dodecyl-2'-hydroxy-5'-methylphenyl) benzotriazole, a mixture of 2-(3'-tert-butyl-2'-hydroxy-5'-(2-isooctyloxycarbonylethyl) phenyl) benzotriazole and 2,2'-methylene-bis[4-(1,1,3,3-tetramethylbutyl)-6-benzotriazol-2-ylphenol], a transesterification reaction product of 2-[3'-tert-butyl-5'-(2-methoxycarbonylethyl)-2'-hydroxyphenyl] benzotriazole with polyethylene glycol 300, and [[R—CH$_2$CH$_2$—COOCH$_2$]$_3$]$_2$— (wherein, R is 3'-tert-butyl-4'-hydroxy-5'-2H-benzotriazol-2-yl-phenyl);

benzophenone compounds such as 2,4-dihydroxybenzophenone, 2-hydroxy-4-methoxybenzophenone, 2-hydroxy-4-octoxybenzophenone, 2-hydroxy-4-decyloxybenzophenone, 2-hydroxy-4-dodecyloxybenzophenone, 2-hydroxy-4-benzyloxybenzophenone, 2,2',4,4'-tetrahydroxybenzophenone and 2,2'-dihydroxy-4,4'-dimethoxybenzophenone;

4-tert-butylphenyl salicylate, phenyl salicylate, octylphenyl salicylate, dibenzoylresorcinol, bis(4-tert-butylbenzoyl) resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl benzoate and 3,5-di-tert-butyl-4-hydroxybenzoate;

hindered amine compounds such as bis (2,2,6,6-tetramethyl piperidyl) sebacate, bis (2,2,6,6-tetramethyl piperidyl) succinate, bis (1,2,2,6,6-pentamethyl) piperidyl) sebacate, bis (1,2,2,6,6-pentamethyl piperidyl) n-butyl-3,5-di-tert-butyl-4-hydroxybenzyl malonate, a condensation product of 1-hydroxyethyl-2,2,6,6-tetramethyl-4-hydroxypiperidine with succinic acid, a condensation product of N,N'-bis-(2,2,6,6-tetramethyl-4-piperidyl) hexamethylenediamine with 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethanediyl) bis (3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethyl-4-piperidyl) 2-n-butyl-2-(2-hydroxy-3,5-di-tert-butylbenzyl) malonate, 3-n-octyl-7,7,9,9-tetramethyl-1,3,8-triazaspiro [4.5] decane-2,4-dione, bis (1-octyloxy-2,2,6,6-tetramethyl piperidyl) sebacate, bis (1-octyloxy-2,2,6,6-tetramethylpiperidyl) succinate, a condensation product of N,N'-bis (2,2,6,6-tetramethyl-4-piperidyl) hexamethylenediamine with 4-morpholino-2,6-dichloro-1,3,5-triazine, a condensation production of 2-chloro-4,6-di-(4-n-butylamino-2,2,6,6-tetramethylpiperidyl)-1,3,5-triazine and 1,2-bis (3-aminopropylamino) ethane, a condensation product of 2-chloro-4,6-di-(4-n-butylamino-1,2,2,6,6-pentamethylpiperidyl)-1,3,5-triazine with 1,2-bis (3-aminopropylamino) ethane, 8-acetyl-3-dodecyl-7,7,9,9-tetramethyl-1,3,8-triazaspiro [4.5] decane-2,4-dione, 3-dodecyl-1-(2,2,6,6-tetramethyl-4-piperidyl) pyrrolidine-2,5-dione and 3-dodecyl-1-(1,2,2,6,6-pentamethyl-4-piperidyl) pyrrolidine-2,5-dione;

oxalamide compounds such as 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis (3-dimethylaminopropyl) oxalamide, a mixture of 2-ethoxy-5-tert-butyl-2'-ethyloxanilide and 2-ethoxy-2'-ethyl-5,4'-di-tert-butyloxanilide, and mixtures of o- and p-methoxy, and o- and p-ethoxy-disubstituted oxalinide;

2-(2-hydroxyphenyl)-1,3,5-triazine compounds such as 2,4,6-tris (2-hydroxy-4-octyloxyphenyl)-1,3,5-triazine, 2-(2-hydroxy-4-octyloxyphenyl)-4,6-bis (2,4-dimethylphenyl)-1,3,5-triazine, 2-(2,4-dihydroxyphenyl)-4,6-bis (2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis (4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxypropyloxy) phenyl]-4,6-bis (2,4-dimethylphenyl)-1,3,5-triazine, 2-[2-hydroxy-4-(2-hydroxy-3-octyloxypropyloxy) phenyl]-4,6-bis (2,4-dimethylphenyl)-1,3,5-triazine and 2-[4-dodecyl/tridecyloxy-(2-hydroxypropyl) oxy-2-hydroxyphenyl]-4,6-bis (2,4-dimethylphenyl)-1,3,5-triazine; and phosphite compounds or phosphonite compounds such as triphenyl phosphite, diphenyl alkyl phosphite, phenyl dialkyl phosphite, tris (nonylphenyl phosphite), trilauryl phosphite, trioctadecyl phosphite, distearyl pentaerythrityl diphosphite, tris-(2,4-di-tert-butylphenyl) phosphite, diisodecylpentaerythrityl diphosphite, bis (2,4-di-tert-butylphenyl) pentaerythrityl diphosphite, bis (2,6-di-tert-butyl-4-methylphenyl) pentaerythrityl diphosphite, bis-isodecyloxypentaerythrityl diphosphite, bis (2,4-di-tert-butyl-6-methylphenyl) pentaerythrityl diphosphite, bis (2,4,6-tri-tert-butylphenyl) pentaerythrityl diphosphite, tristearylsorbityl triphosphate, tetrakis (2,4-di-tert-butylphenyl) 4,4'-biphenylene diphosphonite, 6-isooctyloxy-2,4,8,10-tetra-tert-butyl-12H-dibenzo [d,g]-1,3,2-dioxaphosphocin, 6-fluoro-2,4,8,10-tetra-tert-butyl-12H-methyldibenzo [d,g]-1,3,2-dioxaphosphocine, bis (2,4-di-tert-butyl-6-methylphenyl) methyl phosphite and bis (2,4-di-tert-butyl-6-methylphenyl) ethyl phosphite.

Among them, benzotriazole compounds are preferable.

The amount of the ultraviolet absorber added is preferably 10 to 1,000 ppm, more preferably 100 to 800 ppm, based on the monomer (A). The addition of the ultraviolet absorber tends to suppress the coloration of the liquid containing the monomer and improve the storage stability of the monomer itself.

Examples of other components further include softeners and plasticizers.

Examples of the softeners include rubbers such as natural rubber and synthetic rubber, and elastomers such as thermoplastic elastomers. Such softeners can enhance the softness of the composition for hard tissue repair. Concrete examples of the synthetic rubber include EPT (ethylene-propylene terpolymer). Concrete examples of the thermoplastic elastomer include styrene-based elastomers, vinyl chloride-based elastomers, olefin-based elastomers, polyester-based elastomers, polyimide-based elastomers and urethane-based elastomers.

The molecular weight of the elastomer is usually 1000 to 1,000,000, preferably 2000 to 500,000. The glass transition point (Tg) of the elastomer is usually 20° C. or less, preferably 0° C. or less.

Specific examples of the plasticizers include hydroxycarboxylic acid esters such as esters of citric acid, esters of isocitric acid, esters of tartaric acid, esters of malic acid, esters of lactic acid, esters of glyceric acid and esters of glycolic acid; trimethyl trimellitate, diethylene glycol dibenzoate, diethyl malonate, triethyl acetyl citrate, benzylbutyl phthalate, dipropylene glycol dibenzoate, diethyl adipate, tributyl acetyl citrate, dimethyl sebacate and alkylene glycol diesters.

The addition amount of the softener and the plasticizer may be appropriately determined depending on the type thereof, but is generally 0 to 30% by mass, preferably 0 to 20% by mass, more preferably 0 to 10% by mass in the whole composition for hard tissue repair.

The composition for hard tissue repair of the present invention may contain a preservative, if necessary. Concrete examples of the preservative include methylparaben, methylparaben sodium, ethylparaben, propylparaben, propylparaben sodium, butylparaben, cresol, chlorocresol, resorcinol, 4-n-hexylresorcinol, 3a,4,7,7a-tetrahydro-2-((trichloromethyl)thio)-1H-isoindole-1,3 (2H)-dione, benzalkonium chloride, benzalkonium sodium chloride, benzethonium chloride, benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercury compounds such as phenylmercuric borate, phenylmercuric nitrate and phenylmercuric acetate, and formaldehyde.

Other components further include anti-infectious agents, antibiotics, antimicrobial agents, anti-virus agents, analgesics, a composition containing an analgesic, anorectic drugs, antihelmintic drugs, antiarthritic agents, antiasthmatic drugs, anticonvulsants, antidepressant agents, antidiuretics, antidiarrheal agents, antihistamine drugs, anti-inflammatory drugs, antimigraine drugs, antiemetic agents, antineoplasm drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, awakening drugs, sedative drugs, tranquilizers, cholinergic agents, chemotherapeutic drugs, radio pharmaceuticals, drugs for osteogenic induction, heparin neutralizer agents with bladder stand still, procoagulants, hemostatic agents, xanthine derivatives, hormones, proteins of natural origin or proteins synthesized by genetic engineering, polysaccharides, glycoproteins, lipoproteins, oligonucleotides, antibodies, antigens, vasopressin, vasopressin analogs, epinephrine, selectin, procoagulation toxicants, inhibitors against plasminogen activating factor, platelet activators, bone-forming factors, bone growth factors, synthetic peptides having hemostatic action, and other pharmaceutical or therapeutic components.

The composition for hard tissue repair of the present invention can also be used in drug delivery systems or as regenerative medicine by containing the above other component(s).

Concrete examples of the antimicrobial agents include elemental iodine, solid polyvinylpyrrolidone iodine and polyvinylpyrrolidone iodine; phenol compounds such as tribromophenol, trichlorophenol, tetrachlorophenol, nitrophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol, 2,4-dichloro-3,5-dimethylphenol, 4-chlorothymol, chlorphen, triclosan, fenticlor, phenol, 2-methylphenol, 3-methylphenol, 4-methylphenol, 4-ethylphenol, 2,4-dimethylphenol, 2,5-dimethylphenol, 3,4-dimethylphenol, 2,6-dimethylphenol, 4-n-propylphenol, 4-n-butylphenol, 4-n-amylphenol, 4-tert-amylphenol, 4-n-hexylphenol, 4-n-heptylphenol, monoalkylhalophenols, polyalkylhalophenols, aromatic halophenols, and ammonium salts, alkali metal salts and alkaline earth metal salts thereof; silver nitrate; hexachlorophene; and merbromin.

Examples of the antibiotics include gentamicin, gentamicin sulfate, tobramycin, tobramycin sulfate, amikacin, amikacin sulfate, dibekacin, dibekacin sulfate, vancomycin, vancomycin hydrochloride, fosfomycin, cefazolin, cefazolin sodium, minocycline, clindamycin, colistin, linezolid, tetracycline hydrochloride, tetracycline hydrate, oxytetracycline and erythromycin.

The addition amount of the antibiotic may be appropriately determined depending on the type thereof, but it is usually 0 to 30% by mass, preferably 0 to 20% by mass, more preferably 0 to 10% by mass with respect to 100% by mass of the sum of the polymer (B), the polymerization initiator (C) and the contrast medium (X).

The composition for hard tissue repair of the present invention may contain bone morphogenetic factors, bone growth factors, and other pharmaceutical or therapeutic components for the purpose of promoting tissue repair.

Other components include a perfume. Concrete examples of the perfume include orange oil, grapefruit oil, lemon oil, lime oil, clove oil, wintergreen oil, peppermint oil, peppermint spirits, banana distillate, cucumber distillate, honey distillate, rose water, menthol, anethole, alkyl salicylate, benzaldehyde, monosodium glutamate, ethyl vanillin, thymol and vanillin.

Examples of other components further include inorganic fillers (except for the above-mentioned X-ray contrast medium), organic fillers, organic composite fillers and colorants for the purpose of clarification of visual distinction from surrounding bone tissue, improvement of adhesion, enhancement of physical properties such as compressive strength, or reducing invasiveness to surrounding bone tissue by complementing active radical species.

Concrete examples of the inorganic fillers include metal oxide powder such as bismuth oxide, titanium oxide, zinc oxide and aluminum oxide particles; metal salt powders such as zirconium phosphate; glass fillers such as silica glass, aluminum-containing glass, barium-containing glass, strontium-containing glass and zirconium silicate glass; fillers with sustained silver release, fillers with sustained calcium release; and fillers with sustained fluorine release. From the viewpoint of forming a strong bond between the inorganic filler and the monomer (A) after curing, surface-treated inorganic fillers by a surface treatment such as silane treatment or polymer coating are preferred. These inorganic fillers can be used alone, or two or more inorganic fillers can be used in combination.

Concrete examples of the colorants (each color number is represented as Index by Japanese Color Name), include, Red No. 2 and aluminum lakes thereof, Red No. 3 and aluminum lakes thereof, Red No. 102 and aluminum lakes thereof, Red No. 104-(1) and aluminum lakes or barium lakes thereof, Reds No. 105-(1) and aluminum lakes thereof, Red No. 106 and aluminum lakes thereof, Yellow No. 4 and aluminum lakes or barium lakes or zirconium lakes thereof, Yellow No. 5 and aluminum lakes or barium lakes or zirconium lakes thereof, Green No. 3 and aluminum lakes thereof, Blue No. 1 and aluminum lakes or barium lakes or zirconium lakes thereof, Blue No. 2 and aluminum lakes thereof, Red No.

201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227 and aluminum lakes thereof, Red No. 228, Red No. 230-(1) and aluminum lakes thereof, Red No. 230-(2) and aluminum lakes thereof, Red No. 231 and aluminum lakes thereof, Red No. 232 and aluminum lakes thereof, Orange No. 201, Orange No. 203, Orange No. 204, Orange No. 205 and aluminum lakes or barium lakes or zirconium lakes thereof, Orange No. 206, Orange No. 207 and aluminum lakes thereof, Yellow No. 201, Yellow No. 202-(1) and aluminum lakes thereof, Yellow No. 202-(2) and aluminum lakes thereof, Yellow No. 203 and aluminum lakes or barium lakes or zirconium lakes thereof, Yellow No. 204, Yellow No. 205, Green No. 201 and aluminum lakes thereof, Green No. 202, Green No. 204 and aluminum lakes thereof, Green No. 205 and aluminum lakes or zirconium lakes thereof, Blue No. 201, Blue No. 202 and barium lakes thereof, Blue No. 203, Blue No. 204, Blue No. 205 and aluminum lakes thereof, Brown No. 201 and aluminum lakes thereof, Purple No. 201, Red No. 401 and aluminum lakes thereof, Red No. 404, Red No. 405, Red No. 501, Red No. 502 and aluminum lakes thereof, Red No. 503 and aluminum lakes thereof, Red No. 504 and aluminum lakes thereof, Red No. 505, Red No. 506 and aluminum lakes thereof, Orange No. 401, Orange No. 402 and aluminum lakes or barium lakes thereof, Orange No. 403, Yellow No. 401, Yellow No. 402 and aluminum lakes thereof, Yellow No. 403-(1) and aluminum lakes thereof, Yellow No. 404, Yellow No. 405, Yellow No. 406 and aluminum lakes thereof, Yellow No. 407 and aluminum lakes thereof, Green No. 401, Green No. 402 and aluminum lakes or barium lakes thereof, Blue No. 403, Blue No. 404, Purple No. 401 and aluminum lakes thereof, Black No. 401 and aluminum lakes thereof; chlorophyll, chlorophyllin, malachite green, crystal violet, brilliant green, cobalt phthalocyanine, carotene, vitamin B12 and derivatives derived therefrom.

These colorants can be used alone, or two or more colorants can be used in combination.

The addition amount of the colorant may be appropriately determined depending on the type thereof, and is usually 0 to 5% by mass, preferably 0 to 2% by mass, more preferably 0 to 1% by mass with respect to 100% by mass of the sum of the polymer (B), the polymerization initiator (C) and the contrast medium (X).

[Composition for Hard Tissue Repair]

The composition for hard tissue repair according to the present invention is prepared by mixing the monomer (A), the polymer (B), the polymerization initiator (C), the contrast medium (X) and the other components contained as needed. This composition can be used, for example, by applying to the affected area. In the present invention, the "composition for hard tissue repair" is used for mutual adhesion of hard tissues, filling into hard tissues, adhesion and/or close contact between hard tissues and artifacts such as titanium, ceramics and stainless steel, and adhesion and/or close contact between hard tissues and other tissues such as soft tissues, but does not include adhesion between teeth and filling materials (i.e., dental use).

Upon mixing of these components, the order of mixing is not limited. From the view point that the stability of the composition for hard tissue repair to be obtained is more excellent, it is preferable that, first, the monomer (A) and the polymerization initiator (C) are mixed, and subsequently, the polymer (B) beforehand blended with the contrast medium (X) is mixed. It is more preferable that the monomer (A), the polymerization initiator (C), and the polymer (B) beforehand blended with the contrast medium (X), are mixed simultaneously.

When the composition for hard tissue repair of the present invention contains a polymerization inhibitor, it is preferable that, first, a mixture of the monomer (A) and a polymerization inhibitor is mixed with the polymerization initiator (C), and, subsequently, the polymer (B) beforehand blended with the contrast medium (X) is mixed, from the view point that the stability of the composition to be obtained is more excellent. It is more preferable that a mixture of the monomer (A) and a polymerization inhibitor; the polymerization initiator (C); and the polymer (B) beforehand blended with the contrast medium (X) are mixed simultaneously.

In the composition for hard tissue repair of the present invention, simulated bone penetrability as measured by the following method is preferably 1.0 mm or more, more preferably 1.0 to 6.0 mm. Thus, the composition for hard tissue repair is more excellent in adhesion to bone tissue.

(Method of Measuring Simulated Bone Penetrability)

A simulated bone penetrability is measured by impregnating a polyurethane foam having open cell porous (porosity 95%) with physiological saline (trade name: 0.01 mol/L phosphate buffered physiological saline, manufactured by Wako Pure Chemical Industries, Ltd.), placing a composition at 5 minutes after the composition becomes a soft mass and has no more stringing on the upper surface thereof, applying a pressure load to the composition at a pressure of 75 kPa for 30 seconds, and measuring the penetration or invasion depth (mm) of the composition into the polyurethane foam, as the simulated bone penetrability.

The volume mean particle diameter of all particles (specifically, the polymer (B) when in the form of powder, the contrast medium (X) and other particles) contained in the composition for hard tissue repair of the present invention is preferably 32 μm or less, more preferably 15 to 26 μm. When the volume mean particle diameter of all particles exceeds 26 μm, the above-mentioned simulated bone penetrability is inferior. The method of measuring the volume mean particle diameter is described later in the section "Example".

The content of the contrast medium (X) in all particles contained in the composition for hard tissue repair of the present invention, is preferably 1.0% by mass or more and less than 20% by mass, more preferably 1.5% by mass or more and 19% by mass or less, particularly preferably 2.0% by mass or more and 18% by mass or less.

Prior to curing the composition for hard tissue repair of the present invention, the composition may be sterilized by treatments such as a dry-heat treatment, a treatment using a gas such as steam, ethylene oxide (EO) or hydrogen peroxide, a filtration treatment and a treatment using liquid. Prior to filling of the composition for hard tissue repair of the present invention, the affected area may be disinfected beforehand with a disinfectant such as alcohol. Before the affected area is filled with the composition for hard tissue repair, a pre-treatment may be carried out for the purpose of improving adhesion to the affected area. As the liquid for the pre-treatment, for example, physiological saline is mentioned.

[Kit for Hard Tissue Repair]

When there is a case that the composition for hard tissue repair of the present invention may change in its form and performance over a long period of time and that the effects of the present invention may be impaired, the monomer (A), the polymer (B), the polymerization initiator (C), the contrast medium (X) and all other components may be divided into three or more portions in an optional combination and the divided portions may be stored in three or more members, respectively, as a kit for hard tissue repair. The components may be mixed directly before their use to prepare a composition for hard tissue repair. As a member for storage of the monomer (A) or the polymerization initiator (C), a member for preventing volatilization and scattering thereof is preferable. Concrete examples thereof include a sealable resin container or glass ampoule having a gas barrier property. Concrete examples of the members for packing the polymer (B) include resin containers and glass containers having good sealability that can prevent moisture absorption; and a non-woven resin fabric and a sterile paper with gas permeability, that can be sterilized by a gas such as ethylene oxide (EO) or hydrogen peroxide.

As the kit for hard tissue repair, a kit for hard tissue repair is preferable, wherein the components are divided into three mixtures, i.e., a mixture of the monomer (A) and the other component(s) as required, a mixture of the polymer (B) blended beforehand with the contrast medium (X) and the other component(s) as required, and a mixture of the polymerization initiator (C) and the other component(s) as required; and packed into three separate members, respectively. However, the kit for hard tissue repair is not limited to the above combination. The kit for hard tissue repair may be that, wherein the components may be divided, for example, into four mixtures, i.e., a mixture of the monomer (A) and the other component(s) as required, a mixture of the polymer (B) and the other component(s) as required, a mixture of the contrast medium (X) and the other components as required, and a mixture the polymerization initiator (C) and the other component(s), and packed into four separate members, respectively. The kit for hard tissue repair may be that, wherein the components may be divided into three mixtures, i.e., a mixture of the monomer (A), the contrast medium (X) and the other component(s); a mixture of the polymer (B) and the other component(s) as required; and a mixture of the polymerization initiator (C) and the other component(s), and packed into three separate members, respectively.

The kit for hard tissue repair having three or more members containing these components can be provided as a product.

For the use of a kit for hard tissue repair, it is preferable, for example, that a mixture of the monomer (A) and the other component(s) as required is first mixed with a mixture of the polymerization initiator (C) and the other component(s) and, then, a mixture of the polymer (B) beforehand blended with the contrast medium (X) and the other component(s) as required is mixed thereto. These mixtures may also be mixed, simultaneously. A composition for hard tissue repair having more stable ability can be obtained easily, by the above mixing.

The kit for hard tissue repair may comprise, not only members in which components are stored (for example, a resin container, a glass ampoule), but also members for taking out and mixing the respective components (for example, a cement gun, a mixing container, a mixing dish, a cement injector, a cylinder).

A kit for hard tissue repair may comprises one chamber (as a container for mixing), the inside of which may be separated into three or more parts by a partition wall or a spacer, and each of the components may be accommodated separately in the three or more parts. The kit for hard tissue repair may have a stirring unit for mixing components by operating a stirring blade after bringing the monomer (A) and the polymerization initiator (C) into contact with the polymer (B) beforehand blended with the contrast medium (X) by breaking or moving the partition wall or removing the spacer. Such a kit for hard tissue repair makes mixing operation easier in comparison with the case by taking out each of the components from each container and mixing them. Furthermore, it is also useful in terms of facilitating the operation to use a jig such as a cement gun for directly filling the affected area with the composition from the chamber (mixing container).

A part or all of the polymerization initiator (C) may be previously held in a jig which is used for application of the composition for hard tissue repair to the affected part of hard tissue such as bones and cartilages, as well as soft tissue and the other artificial products such as titanium, ceramics or stainless steel, etc. In this case, a composition for hard tissue repair is prepared by bringing the monomer (A), the polymer powder (B) and the other component(s) as required into direct contact with the jig just before its use, and the composition thus prepared alone is filled in the affected part, as it is.

Examples of the jig for filling the affected area with the composition for hard tissue repair include a cement gun.

The kit for hard tissue repair may have, for example, an antiseptic solution such as an alcohol described above or a solution for pretreatment for the purpose of improving adhesion.

When components are packed for the kit for hard tissue repair, the components may be sterilized with an electromagnetic wave such as visible light, preferably under the conditions wherein the components do not deteriorate (for example, the monomer does not cure).

EXAMPLES

Hereinafter, the present invention will be more specifically described based on the examples, but the present invention is not limited to these examples.

(1) Specific Surface Area

The specific surface area of the polymer powder was measured by a nitrogen gas adsorption method under liquid nitrogen temperature, using an apparatus "BELSORP-mini" (manufactured by Microtrack Bel) by performing vacuum degassing at room temperature as pretreatment.

(2) Weight Average Molecular Weight (Mw)

The polymer powder was dissolved in a special grade reagent tetrahydrofuran (manufactured by Wako Pure Chemical Industries, Ltd.), and this solution was filtered through a hydrophobic 0.45 µm polytetrafluoroethylene filter. The solution after filtration was used as a sample, and the weight average molecular weight (Mw) of the polymer powder was measured (as a standard polystyrene-equivalent value) using a high performance liquid chromatography apparatus (manufactured by Shimadzu Corporation, LC-10AD), a separation column (PLgel (10 µm) MIXED-B×2), and a detector (manufactured by Shodex, RI-101).

(3) Volume Mean Particle Diameter D50

A special grade reagent methanol (manufactured by Wako Pure Chemical Industries, Ltd., solvent refractive index: 1.33) or a 0.2% by mass sodium hexametaphosphate aqueous solution (manufactured by Wako Pure Chemical Industries, Ltd., solvent refractive index: 1.33) was used as a dispersion solvent, and the polymer powder or the contrast medium was dispersed for 5 minutes (output 25 W) by an ultrasonic homogenizer. This dispersion was used as a sample, and the volume mean particle diameter D50 of the polymer powder, the contrast medium and all particles included in the composition were measured using a particle diameter distribution analyzer (manufactured by Microtrac Bel, Microtrac MT3300EXII) under the concentration condition within the device Loading Index suitable amount range and at a circulation rate of 50% (when 100%, 65 mUsec).

(4) Simulated Bone Penetrability

Regarding "Simulated bone penetrability", a bone model simulating cancellous bone composed of a polyurethane foam having open cell porous (manufactured by Human Body Corp, trade name: SAW1522-507, porosity: 95%) was impregnated with physiological saline (manufactured by Wako Pure Chemical Industries, Ltd., trade name: 0.01 mol/L phosphate buffered physiological saline), a composition at 5 minutes after the composition became a soft mass and had no more stringiness was placed on the upper surface of the polyurethane foam. A load was then applied to the composition at a pressure of 75 kPa for 30 seconds, and the penetration depth (mm) was measured.

(5) Adhesion to Pig Femur

Regarding "Adhesion to pig femur", an appropriate amount of a composition at 5 minutes after the composition became a soft mass and had no more stringiness was filled in the intrathecal space of an edible pig femur, and the filled composition was cured for 24 hours under conditions of a temperature of 37° C. and a relative humidity RH of 95% while applying a load of 200 g. Then, the value (N) of the load necessary for boring a hole therethrough to hollow out the composition from the pig femur at a rate of 5 mm/min was measured. The evaluation method was carried out by referring to "Canadian Journal of Surgery, 54 (2011) 33-38, Stephen Hunt, Craig Stone, Shane Seal". The edible pig femur was cut in advance to a length of 10 mm, and the intrathecal cavity was thoroughly washed with physiological saline (manufactured by Wako Pure Chemical Industries, Ltd., trade name: 0.01 mol/L phosphate buffered physiological saline), and it was confirmed before their uses that the inner diameter of the intrathecal space (average value of the minimum value and the maximum value) was in the range of 10 to 25 mm and that there were no scratches or cracks.

Examples 1a to 6a, Comparative Examples 1a to 6a

In Examples 1a to 6a and Comparative Examples 1a to 6a, methyl methacrylate as the monomer (A); polymethyl methacrylate (specific surface area=0.32 $m^2/g$, Mw=121,000, volume mean particle diameter D50=21.9 μm) as the spherical polymer powder (b1); polymethyl methacrylate (specific surface area=2.9 $m^2/g$, Mw=442,000, volume mean particle diameter D50=21.3 μm) as the indefinite shape polymer powder (b3); a mixture of 85% by mass of partially oxidized tributyl boron and 15% by mass of ethanol (manufactured by Mitsui Chemicals, Inc., part number BC-S1i) as the polymerization initiator (C) (the total of the polymerization initiator (C) is taken as 100% by mass); and barium sulfate (manufactured by Sakai Chemical Industry Co., Ltd.) as the contrast medium (X), were used.

First, the polymer (B) and the contrast medium (X) were uniformly dispersed at the blending ratio shown in Tables 1 and 2 to prepare a mixture, while a mixture of the monomer (A) and the polymerization initiator (C) was prepared in a 5 mL glass sample tube as a separate step. Then, these two mixtures were mixed at 23° C. for 60 seconds using a polypropylene container (manufactured by Shofu Co., Ltd., trade name: tray resin blender) and a silicon rubber spatula. The resulting mixture was allowed to stand for an appropriate time to obtain a composition for hard tissue repair which became a soft mass without stringing. This composition was used to evaluate the simulated bone penetrability and the adhesion to pig femur. The results are shown in Tables 1 and 2.

The blending ratio shown in the parentheses of each component in the table is a ratio (parts by mass) based on 100 parts by mass of the sum of the components (A) to (C). The blending ratio of the components (b1) and (b3) is a ratio (% by mass) on the basis of 100% by mass of the polymer powder (B).

TABLE 1

| | Composition for hard tissue repair (Parts by mass) | | MW | Volume mean particle diameter D50 (μm) | Volume mean particle diameter D50 of all particles (μm) | Simulated bone penetrability (mm) | Adhesion to pig femur (N) |
|---|---|---|---|---|---|---|---|
| Example 1a | Monomer (A) | 2.82 g (33.2) | — | — | 23.3 | 1.22 | 769 |
| | Polymer (B) | 5.40 g (63.6) | 184 × $10^3$ | 22.3 | | | |
| | (b1) | 77.8% | 121 × $10^3$ | 21.9 | | | |
| | (b3) | 22.2% | 442 × $10^3$ | 21.3 | | | |
| | Polymerization initiator(C) | 0.27 g (3.2) | — | — | | | |
| | Contrast medium (X) | 0.6 g (7.1) | — | 5.7 | | | |
| Example 2a | Monomer (A) | 2.82 g (33.2) | — | — | 22.9 | 1.08 | 818 |
| | Polymer (B) | 5.40 g (63.6) | 184 × $10^3$ | 22.3 | | | |
| | (b1) | 77.8% | 121 × $10^3$ | 21.9 | | | |
| | (b3) | 22.2% | 442 × $10^3$ | 21.3 | | | |
| | Polymerization initiator(C) | 0.27 g (3.2) | — | — | | | |
| | Contrast medium (X) | 0.6 g (7.1) | — | 7.2 | | | |
| Example 3a | Monomer (A) | 2.82 g (33.2) | — | — | 21.9 | 1.33 | 788 |
| | Polymer (B) | 5.40 g (63.6) | 184 × $10^3$ | 22.3 | | | |
| | (b1) | 77.8% | 121 × $10^3$ | 21.9 | | | |
| | (b3) | 22.2% | 442 × $10^3$ | 21.3 | | | |
| | Polymerization initiator(C) | 0.27 g (3.2) | — | — | | | |
| | Contrast medium (X) | 0.6 g (7.1) | — | 12.0 | | | |
| Example 4a | Monomer (A) | 2.82 g (33.2) | — | — | 20.5 | 1.81 | 1085 |
| | Polymer (B) | 5.40 g (63.6) | 183 × $10^3$ | 19.6 | | | |
| | (b1) | 82.8% | 121 × $10^3$ | 21.9 | | | |
| | (b3) | 17.2% | 442 × $10^3$ | 21.3 | | | |
| | Polymerization initiator(C) | 0.27 g (3.2) | — | — | | | |
| | Contrast medium (X) | 0.6 g (7.1) | — | 5.7 | | | |
| Example 5a | Monomer (A) | 2.82 g (33.2) | — | — | 20.2 | 2.10 | 1692 |
| | Polymer (B) | 5.40 g (63.6) | 176 × $10^3$ | 20.1 | | | |
| | (b1) | 82.8% | 121 × $10^3$ | 21.9 | | | |

TABLE 1-continued

|  | Composition for hard tissue repair (Parts by mass) |  | MW | Volume mean particle diameter D50 (μm) | Volume mean particle diameter D50 of all particles (μm) | Simulated bone penetrability (mm) | Adhesion to pig femur (N) |
| --- | --- | --- | --- | --- | --- | --- | --- |
|  | (b3) | 17.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 7.2 |  |  |  |
| Example 6a | Monomer (A) | 2.82 g (33.2) | — | — | 19.5 | 3.50 | 2172 |
|  | Polymer (B) | 5.40 g (63.6) | 180 × 10³ | 20.0 |  |  |  |
|  | (b1) | 82.8% | 121 × 10³ | 21.9 |  |  |  |
|  | (b3) | 17.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 12.0 |  |  |  |

TABLE 2

|  | Composition for hard tissue repair (Parts by mass) |  | MW | Volume mean particle diameter D50 (μm) | Volume mean particle diameter D50 of all particles (μm) | Simulated bone penetrability (mm) | Adhesion to pig femur (N) |
| --- | --- | --- | --- | --- | --- | --- | --- |
| Comparative Example 1a | Monomer (A) | 2.82 g (33.2) | — | — | 25.8 | 0.30 | 339 |
|  | Polymer (B) | 5.40 g (63.6) | 184 × 10³ | 22.3 |  |  |  |
|  | (b1) | 77.8% | 121 × 10³ | 21.9 |  |  |  |
|  | (b3) | 22.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 0.57 |  |  |  |
| Comparative Example 2a | Monomer (A) | 2.82 g (33.2) | — | — | 25.9 | 0.32 | 371 |
|  | Polymer (B) | 5.40 g (63.6) | 184 × 10³ | 22.3 |  |  |  |
|  | (b1) | 77.8% | 121 × 10³ | 21.9 |  |  |  |
|  | (b3) | 22.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 0.86 |  |  |  |
| Comparative Example 3a | Monomer (A) | 2.82 g (33.2) | — | — | 24.0 | 0.31 | 357 |
|  | Polymer (B) | 5.40 g (63.6) | 184 × 10³ | 22.3 |  |  |  |
|  | (b1) | 77.8% | 121 × 10³ | 21.9 |  |  |  |
|  | (b3) | 22.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 2.2 |  |  |  |
| Comparative Example 4a | Monomer (A) | 2.82 g (33.2) | — | — | 22.9 | 0.41 | 322 |
|  | Polymer (B) | 5.40 g (63.6) | 181 × 10³ | 20.0 |  |  |  |
|  | (b1) | 77.8% | 121 × 10³ | 21.9 |  |  |  |
|  | (b3) | 22.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 0.86 |  |  |  |
| Comparative Example 5a | Monomer (A) | 2.82 g (33.2) | — | — | 21.7 | 0.66 | 402 |
|  | Polymer (B) | 5.40 g (63.6) | 180 × 10³ | 20.4 |  |  |  |
|  | (b1) | 77.8% | 121 × 10³ | 21.9 |  |  |  |
|  | (b3) | 22.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 2.2 |  |  |  |
| Comparative Example 6a | Monomer (A) | 2.82 g (33.2) | — | — | 32.1 | 0.18 | 332 |
|  | Polymer (B) | 5.40 g (63.6) | 180 × 10³ | 20.4 |  |  |  |
|  | (b1) | 77.8% | 121 × 10³ | 21.9 |  |  |  |
|  | (b3) | 22.2% | 442 × 10³ | 21.3 |  |  |  |
|  | Polymerization initiator(C) | 0.27 g (3.2) | — | — |  |  |  |
|  | Contrast medium (X) | 0.6 g (7.1) | — | 2.2 |  |  |  |

As shown in Tables 1 and 2, the compositions for hard tissue repair of Examples 1a to 6a using barium sulfate having a large volume mean particle diameter as the contrast medium (X) were excellent in the simulated bone penetrability and the adhesion to pig femurs. This composition for hard tissue repair can be expected to have improved adhesion when used as a bone cement for treatment of patients.

In contrast, the compositions for hard tissue repair of Comparative Examples 1a to 6a using barium sulfate having a small volume mean particle diameter as the contrast medium (X) were inferior in the simulated bone penetrability and the adhesion to pig femur. In addition, the composition for hard tissue repair of Comparative Example 6a having the largest volume mean particle diameter of all particles contained in the composition for hard tissue repair among Comparative Examples 1a to 6a was most inferior in the simulated bone penetrability and the adhesion to pig femur. It is understood from this result that if the volume mean particle diameter of all particles contained in the composition for hard tissue repair is too large, there is a tendency for the simulated bone penetrability and the adhesion to pig femur to decrease on the contrary.

Example 1b and Comparative Example 1b

A composition for hard tissue repair was prepared and evaluated in the same manner as in Example 4a except that zirconia (trade name: Zirconium (IV) Oxide manufactured by Kojundo Chemical Lab. Co., Ltd. and trade name:

Zirconium (IV) manufactured by Aldrich) having a volume mean particle diameter shown in Table 3 was used instead of barium sulfate as the contrast medium (X). The results are shown in Table 3.

TABLE 3

| | Composition for hard tissue repair (Parts by mass) | | MW | Volume mean particle diameter D50 (μm) | Volume mean particle diameter D50 of all particles (μm) | Simulated bone penetrability (mm) | Adhesion to pig femur (N) |
|---|---|---|---|---|---|---|---|
| Example 1b | Monomer (A) | 2.82 g (33.2) | — | — | 19.9 | 1.80 | 1117 |
| | Polymer (B) | 5.40 g (63.6) | $180 \times 10^3$ | 20.0 | | | |
| | (b1) | 82.8% | $121 \times 10^3$ | 21.9 | | | |
| | (b3) | 17.2% | $442 \times 10^3$ | 21.3 | | | |
| | Polymerization initiator(C) | 0.27 g (3.2) | — | — | | | |
| | Contrast medium (X) | 0.6 g (7.1) | — | 5.0 | | | |
| Comparative Example 1b | Monomer (A) | 2.82 g (33.2) | — | — | 20.2 | 0.32 | 347 |
| | Polymer (B) | 5.40 g (63.6) | $180 \times 10^3$ | 20.0 | | | |
| | (b1) | 82.8% | $121 \times 10^3$ | 21.9 | | | |
| | (b3) | 17.2% | $442 \times 10^3$ | 21.3 | | | |
| | Polymerization initiator(C) | 0.27 g (3.2) | — | — | | | |
| | Contrast medium (X) | 0.6 g (7.1) | — | 1.0 | | | |

As shown in Table 3, in the case where the contrast medium (X) was changed from barium sulfate to zirconia, the composition for hard tissue repair of Example 1b using zirconia having a large volume mean particle diameter as the contrast medium (X) was also excellent in the simulated bone penetrability and the adhesion to pig femur. In contrast, the composition for hard tissue repair of Comparative Example 1b using zirconia having a small volume mean particle diameter as the contrast medium (X) was inferior in the simulated bone penetrability and the adhesion to pig femur.

Examples 1c to 3c and Comparative Examples 1c to 3c

A composition for hard tissue repair was prepared and evaluated in the same manner as in Example 4a, except that benzoyl peroxide (manufactured by Aldrich, trade name: Luperox (registered trademark) A75) was used in the blending amount shown in Tables 4 and 5 instead of the alkylborane type polymerization initiator as the polymerization initiator (C); 0.5% by mass of N,N-dimethyl-p-toluidine was added to methyl methacrylate as the monomer (A); and the volume mean particle diameter of barium sulfate was changed as shown in Tables 4 and 5. The results are shown in Tables 4 and 5.

TABLE 4

| | Composition for hard tissue repair (Parts by mass) | | MW | Volume mean particle diameter D50 (μm) | Volume mean particle diameter D50 of all particles (μm) | Simulated bone penetrability (mm) | Adhesion to pig femur (N) |
|---|---|---|---|---|---|---|---|
| Example 1c | Monomer (A) | 2.81 g (34.2) | — | — | 20.5 | 1.60 | 926 |
| | Polymer (B) | 5.40 g (65.6) | $183 \times 10^3$ | 19.6 | | | |
| | (b1) | 82.8% | $121 \times 10^3$ | 21.9 | | | |
| | (b3) | 17.2% | $442 \times 10^3$ | 21.3 | | | |
| | Polymerization initiator(C) | 0.015 g (0.2) | — | — | | | |
| | Contrast medium (X) | 0.6 g (7.1) | — | 5.7 | | | |
| Example 2c | Monomer (A) | 2.81 g (34.2) | — | — | 20.2 | 1.90 | 1113 |
| | Polymer (B) | 5.40 g (65.6) | $176 \times 10^3$ | 20.1 | | | |
| | (b1) | 82.8% | $121 \times 10^3$ | 21.9 | | | |
| | (b3) | 17.2% | $442 \times 10^3$ | 21.3 | | | |
| | Polymerization initiator(C) | 0.015 g (0.2) | — | — | | | |
| | Contrast medium (X) | 0.6 g (7.1) | — | 7.2 | | | |
| Example 3c | Monomer (A) | 2.81 g (34.2) | — | — | 19.5 | 1.78 | 958 |
| | Polymer (B) | 5.40 g (65.6) | $180 \times 10^3$ | 20.0 | | | |
| | (b1) | 82.8% | $121 \times 10^3$ | 21.9 | | | |
| | (b3) | 17.2% | $442 \times 10^3$ | 21.3 | | | |
| | Polymerization initiator(C) | 0.015 g (0.2) | — | — | | | |
| | Contrast medium (X) | 0.6 g (7.1) | — | 12.0 | | | |

TABLE 5

|  | Composition for hard tissue repair (Parts by mass) |  | MW | Volume mean particle diameter D50 (μm) | Volume mean particle diameter D50 of all particles (μm) | Simulated bone penetrability (mm) | Adhesion to pig femur (N) |
| --- | --- | --- | --- | --- | --- | --- | --- |
| Comparative Example 1c | Monomer (A) | 2.81 g (34.2) | — | — | 23.1 | 0.59 | 406 |
|  | Polymer (B) | 5.40 g (65.6) | 182 × 10³ | 20.3 |  |  |  |
|  | (b1) | 82.2% | 121 × 10³ | 21.9 |  |  |  |
|  | (b3) | 17.2% | 442 × 10³ | 21.3 |  |  |  |
|  | Polymerization initiator(C) | 0.015 g (0.2) | — | — |  |  |  |
|  | Contrast medium (X) | 0.6 g (7.1) | — | 0.57 |  |  |  |
| Comparative Example 2c | Monomer (A) | 2.81 g (34.2) | — | — | 22.9 | 0.44 | 411 |
|  | Polymer (B) | 5.40 g (65.6) | 181 × 10³ | 20.0 |  |  |  |
|  | (b1) | 82.8% | 121 × 10³ | 21.9 |  |  |  |
|  | (b3) | 17.2% | 442 × 10³ | 21.3 |  |  |  |
|  | Polymerization initiator(C) | 0.015 g (0.2) | — | — |  |  |  |
|  | Contrast medium (X) | 0.6 g (7.1) | — | 0.86 |  |  |  |
| Comparative Example 3c | Monomer (A) | 2.81 g (34.2) | — | — | 21.7 | 0.66 | 356 |
|  | Polymer (B) | 5.40 g (65.6) | 180 × 10³ | 20.4 |  |  |  |
|  | (b1) | 82.8% | 121 × 10³ | 21.9 |  |  |  |
|  | (b3) | 17.2% | 442 × 10³ | 21.3 |  |  |  |
|  | Polymerization initiato r(C) | 0.015 g (0.2) | — | — |  |  |  |
|  | Contrast medium (X) | 0.6 g (7.1) | — | 2.2 |  |  |  |

As shown in Tables 4 and 5, in the case where the polymerization initiator (C) was changed from the alkylborane type polymerization initiator to benzoyl peroxide, the compositions for hard tissue repair of Examples 1c to 3c using barium sulfate having a large volume mean particle diameter as the contrast medium (X) were also excellent in the simulated bone penetrability and the adhesion to pig femur. In contrast, the compositions for hard tissue repair of Comparative Examples 1c to 3c using barium sulfate having a small volume mean particle diameter as the contrast medium (X) were inferior in the simulated bone penetrability and the adhesion to pig femur.

In addition, when Examples 1c to 3c using benzoyl peroxide as the polymerization initiator (C) and Examples 4a to 6a using the alkylborane type polymerization initiator as the polymerization initiator (C) were compared, respectively, the simulated bone penetrability and the adhesion to pig femur were more excellent in Examples 4a to 6a. It is understood from this result that organic boron compounds such as the alkylborane type polymerization initiators were more preferred as the polymerization initiator (C) in terms of the adhesion than organic peroxides such as benzoyl peroxide.

Example 1d and Comparative Example 1d

A composition for hard tissue repair was prepared and evaluated in the same manner as in Example 1c except that zirconia (trade name: Zirconium (IV) Oxide manufactured by Kojundo Chemical Lab. Co., Ltd. and trade name: Zirconium (IV) manufactured by Aldrich) having a volume mean particle diameter shown in Table 6 was used instead of barium sulfate as the contrast medium (X). The results are shown in Table 6.

TABLE 6

|  | Composition for hard tissue repair (Parts by mass) |  | MW | Volume mean particle diameter D50 (μm) | Volume mean particle diameter D50 of all particles (μm) | Simulated bone penetrability (mm) | Adhesion to pig femur (N) |
| --- | --- | --- | --- | --- | --- | --- | --- |
| Example 1d | Monomer (A) | 2.81 g (34.2) | — | — | 19.9 | 1.65 | 1006 |
|  | Polymer (B) | 5.40 g (65.6) | 180 × 10³ | 20.0 |  |  |  |
|  | (b1) | 82.8% | 121 × 10³ | 21.9 |  |  |  |
|  | (b3) | 17.2% | 442 × 10³ | 21.3 |  |  |  |
|  | Polymerization initiator(C) | 0.015 g (0.2) | — | — |  |  |  |
|  | Contrast medium (X) | 0.6 g (7.1) | — | 5.0 |  |  |  |
| Comparative Example 1d | Monomer (A) | 2.81 g (34.2) | — | — | 20.2 | 0.74 | 366 |
|  | Polymer (B) | 5.40 g (65.6) | 180 × 10³ | 20.0 |  |  |  |
|  | (b1) | 82.8% | 121 × 10³ | 21.9 |  |  |  |
|  | (b3) | 17.2% | 442 × 10³ | 21.3 |  |  |  |
|  | Polymerization initiator(C) | 0.015 g (0.2) | — | — |  |  |  |
|  | Contrast medium (X) | 0.6 g (7.1) | — | 1.0 |  |  |  |

As shown in Table 6, in the case where benzoyl peroxide was used as the polymerization initiator (C) and zirconia was used as the contrast medium (X), the composition for hard tissue repair of Example 1d using zirconia having a large volume mean particle diameter as the contrast medium (X) was also excellent in the simulated bone penetrability and the adhesion to pig femur. In contrast, the composition for hard tissue repair of Comparative Example 1 d using zirconia having a small volume mean particle diameter as the contrast medium (X) was inferior in the simulated bone penetrability and the adhesion to pig femur.

INDUSTRIAL APPLICABILITY

The composition for hard tissue repair according to the present invention is useful for, for example, mutual adhesion between hard tissues, filling into hard tissues, adhesion between hard tissues and artifacts such as titanium, ceramics and stainless steel, and adhesion between hard tissues and other tissues such as soft tissues. In addition, the composition for hard tissue repair according to the present invention is useful, for example, as a bone cement used for fixing an artificial joint with a hard tissue such as bone and cartilage, a filler for a bone defect, a bone filling material and an artificial bone.

The invention claimed is:

1. A composition for hard tissue repair comprising a monomer (A), a polymer (B), a polymerization initiator (C) and a contrast medium (X) having a volume mean particle diameter of 3 μm or more,
   wherein the monomer (A) is a methyl methacrylate,
   wherein the polymer (B) comprises:
   a polymer powder (b1) having a specific surface area of 0.05 to 0.5 $m^2/g$, and,
   a polymer powder (b2) having a specific surface area of 0.51 to 1.2 $m^2/g$ and/or a polymer powder (b3) of particles having a specific surface area of 1.5 to 4.5 $m^2/g$,
   wherein the initiator (C) is a partially oxidized trialkylboron which contains ethanol but does not contain an aprotic solvent, and
   wherein a volume mean particle diameter of all particles contained in the composition for hard tissue repair is 15 to 26 μm.

2. The composition for hard tissue repair according to claim 1, wherein the contrast medium (X) is barium sulfate or zirconia.

3. The composition for hard tissue repair according to claim 1, wherein the polymer (B) is a (meth)acrylate-based polymer.

4. The composition for hard tissue repair according to claim 1, comprising 10 to 45 parts by mass of the monomer (A), 54.9 to 80 parts by mass of the polymer (B) and 0.1 to 10 parts by mass of the polymerization initiator (C) (the sum of the components (A) to (C) is taken as 100 parts by mass), and 0.5 to 70 parts by mass of the contrast medium (X).

5. The composition for hard tissue repair according to claim 1, wherein the volume mean particle diameter of the contrast medium (X) is 3.0 to 25.1 μm.

6. A kit for hard tissue repair comprising three or more members, in which each of the components of the monomer (A), the polymer (B), the polymerization initiator (C) and the contrast medium (X) of the composition for hard tissue repair according to claim 1 are divided and contained in the members in an optional combination.

* * * * *